(12) United States Patent
Jauregui et al.

(10) Patent No.: US 11,524,204 B2
(45) Date of Patent: Dec. 13, 2022

(54) DEVICE FOR SENSING FORCE AND MOVEMENT IN AN ACTION PERFORMED BY A SUBJECT; A SYSTEM AND METHOD FOR CORRECTING THE FORCE AND MOVEMENT OF THE ACTION

(71) Applicant: BIO-SENSING SOLUTIONS, S.L., Barcelona (ES)

(72) Inventors: Ricardo Jauregui, Barcelona (ES); Silvia Raga, Barcelona (ES); Marco Conti, Barcelona (ES); Giovanni Vergani, Barcelona (ES); Giorgio Pedretti, Barcelona (ES); Alejandro Rodriguez, Barcelona (ES); Alessandro Castagna, Barcelona (ES); Raffaele Garofalo, Barcelona (ES)

(73) Assignee: BIO-SENSING SOLUTIONS, S.L., Barcelona (ES)

( * ) Notice: Subject to any disclaimer, the term of this patent is extended or adjusted under 35 U.S.C. 154(b) by 330 days.

(21) Appl. No.: 16/636,763

(22) PCT Filed: Aug. 10, 2018

(86) PCT No.: PCT/ES2018/070554
§ 371 (c)(1),
(2) Date: Feb. 5, 2020

(87) PCT Pub. No.: WO2019/030423
PCT Pub. Date: Feb. 14, 2019

(65) Prior Publication Data
US 2020/0164243 A1 May 28, 2020

(30) Foreign Application Priority Data
Aug. 11, 2017 (ES) .............................. ES201731028

(51) Int. Cl.
*A63B 21/00* (2006.01)
*G16H 20/30* (2018.01)
(Continued)

(52) U.S. Cl.
CPC ...... *A63B 21/4013* (2015.10); *A63B 21/4001* (2015.10); *A63B 21/4035* (2015.10);
(Continued)

(58) Field of Classification Search
CPC . A63B 21/02; A63B 21/4001; A63B 21/4013; A63B 21/4019; A63B 21/4021;
(Continued)

(56) References Cited

U.S. PATENT DOCUMENTS

| | | | |
|---|---|---|---|
| 5,433,688 A | * | 7/1995 | Davies ................. A63B 21/151 |
| | | | 482/126 |
| 5,538,486 A | * | 7/1996 | France ............... A63B 21/4035 |
| | | | 482/121 |

(Continued)

FOREIGN PATENT DOCUMENTS

| | | | | |
|---|---|---|---|---|
| WO | 2011041678 A1 | | 4/2011 | |
| WO | WO-2011041678 A1 | * | 4/2011 | ............. A61B 5/224 |

(Continued)

*Primary Examiner* — Sundhara M Ganesan
(74) *Attorney, Agent, or Firm* — Hayes Soloway PC

(57) ABSTRACT

The device comprises a belt (3) on which is mounted a first sensing module (4), with: a) a hitch (6) for connecting a recovery component part (7) such as a spring; b) a first movement sensing unit (8) to detect 3D movement; c) a force sensing unit (9) to detect the force exerted by the recovery component part (7) upon the hitch (6); in which the movement and force data are processed and sent wirelessly via a data transmission unit (11); and d) first means of closure (13,14), to close the belt (3) to a required dimension. Allows simultaneous and coordinated consideration of force and movement data.

14 Claims, 9 Drawing Sheets

(51) Int. Cl.
   *A63B 71/06* (2006.01)
   *A63B 24/00* (2006.01)
   *G16H 40/63* (2018.01)
   *A63B 21/072* (2006.01)

(52) U.S. Cl.
   CPC ...... *A63B 21/4043* (2015.10); *A63B 71/0622* (2013.01); *G16H 20/30* (2018.01); *G16H 40/63* (2018.01); *A63B 21/0724* (2013.01); *A63B 2024/0012* (2013.01); *A63B 2071/0627* (2013.01); *A63B 2220/40* (2013.01); *A63B 2220/51* (2013.01); *A63B 2220/836* (2013.01); *A63B 2225/20* (2013.01); *A63B 2225/50* (2013.01)

(58) Field of Classification Search
   CPC ............ A63B 21/4035; A63B 21/4043; A63B 21/0724; A63B 2024/0012; A63B 2071/0627; A63B 2220/40; A63B 2220/51; A63B 2220/836; A63B 2225/20; A63B 2225/50; A63B 24/0003; A63B 71/0622; G16H 20/30; G16H 40/63
   See application file for complete search history.

(56) References Cited

U.S. PATENT DOCUMENTS

| 9,135,347 | B2 * | 9/2015 | Damman | G06Q 10/10 |
| 2011/0092337 | A1 | 4/2011 | Srinivasan et al. | |
| 2011/0306471 | A1 * | 12/2011 | Huang | A61B 5/1114 |
| | | | | 482/44 |
| 2014/0255890 | A1 * | 9/2014 | Kovach | G16H 40/63 |
| | | | | 434/257 |
| 2017/0304679 | A1 * | 10/2017 | Orfield | A63B 21/0724 |

FOREIGN PATENT DOCUMENTS

| WO | WO-2012052769 A1 * | 4/2012 | ....... A63B 21/00043 |
| WO | 2012085502 A1 | 6/2012 | |
| WO | WO-2012085502 A1 * | 6/2012 | ....... A63B 21/00149 |

* cited by examiner

DEVICE FOR SENSING FORCE AND MOVEMENT IN AN ACTION PERFORMED BY A SUBJECT; A SYSTEM AND METHOD FOR CORRECTING THE FORCE AND MOVEMENT OF THE ACTION

CROSS-REFERENCE TO RELATED APPLICATIONS AND PRIORITY

This patent application claims priority from PCT Patent Application No. PCT/ES2018/070554 filed Aug. 10, 2018, which claims priority from ES Patent Application No. P201731028 filed Aug. 11, 2017. Each of these patent applications are herein incorporated by reference in its/their entirety.

OBJECT OF THE INVENTION

The invention can be included within the health sector, in particular, within the musculoskeletal rehabilitation of patients with movement problems in certain joints. More specifically, according to different aspects, the invention has as its object: a device to sense force and movement in an action performed by a subject, preferably in a rehabilitation action performed by an injured patient; a system and a method to correct the force and movement of the action. The invention may also be applied within the sport, for example to improve training or to strengthen joints and muscles. The invention may also be applied in other fields: for example, in the design and use of consoles that simulate certain sports or physical activities, or as a teaching tool, etc.

BACKGROUND OF THE INVENTION

Currently, there are a large number of patients who require musculoskeletal rehabilitation treatment by a rehabilitation physician and a physiotherapist. Thus, a patient is understood to be any person with any symptom of both acute and chronic ailments, or temporary or permanent mobility problems that requires musculoskeletal rehabilitation treatment.

Currently, most patients who have any symptoms of muscular ailments go to the rehabilitation doctor, who makes a diagnosis, which is transferred to the physiotherapist who must assign a rehabilitation therapy or treatment based on actions or exercises. Usually the patients begin by performing actions supervised by the physiotherapist, and then continue to perform these actions, preferably in their homes, without any supervision.

In addition, in the case of exercises with weight or elastic resistance, where the strength exerted by the patient is relevant, physiotherapists do not have tools that allow them to supervise the execution of exercises that involve strength. The main problem is that both, patients and physiotherapists have no way of ensuring that they perform the actions correctly during the supervision time, or of confirming whether the assigned actions are appropriate.

Without supervision, rehabilitation exercises are not efficient, as in these cases, 80% of patients tend to stop doing the exercises recommended by the physiotherapist. The main reason is that the patient is in a situation where he does not recognize, or does not remember, whether he is doing the action correctly. In this way, patients either abandon rehabilitation or take incorrect actions that may increase the problem rather than solve it.

In particular, it is important to note that adherence to the exercises recommended by the physiotherapist is currently low and ineffective according to various studies showing that only 20% of patients complete the treatments. Additionally, in the first 20 weeks of treatment, 25% of patients stop following all actions, and in the second 20 weeks this increases to 40%, as well as 35% of patients do not complete actions in the first 20 weeks.

In order to solve these problems, a system and a method for the proprioceptive stimulation of movement is known, and its characterization includes: a component to measure the proprioceptive action and another component for the characterization of movement. Both components are coupled so that they can be used on the patient's upper and lower extremities that show a motor deficit. Both the system and the method can be applied in healthcare for patients with musculoskeletal problems, particularly in neurorehabilitation, in activities of science, in sports, in products aimed at recreational market segments (for example dance, video games, interactive television, 3D cinema) and to improve motor and sports performance.

This system and method, although it allows monitoring the movement and notifying the patient if the action is performed correctly, is designed to measure only mobility parameters compared to a set of standardized and equal parameters for all users. The use of these solutions defines the same criteria for all users, which leads to possible injuries due to the lack of customization of the exercise. Another disadvantage of this method and system is that it is not capable of measuring the force, or the work, performed by the patient during the action, being this a key parameter for a rehabilitation process.

It is important to note that there are movement sensors and force sensors, but in no case are they combined and synchronized in order to obtain a personalized model of the movement and, much less, of a process of musculoskeletal rehabilitation.

DESCRIPTION OF THE INVENTION

The invention refers, according to a first aspect, to a device for sensing force and movement in an action performed by a subject. Preferably, the action is an action that is part of a rehabilitation exercise.

The device is based on allowing simultaneous and coordinated measurement of both force and movement, as well as wirelessly transmitting information on force and movement measurements, for its analysis.

In particular, the device comprises a belt as well as a first sensing module, mounted on the belt, which in turn comprises a first housing, which protrudes from the belt. Various components parts are mounted in the first housing, as shown below:

a hitch, intended to be connected to a recovery element, which exerts a recovery force on the hitch when activated by the patient during the rehabilitation exercise;
 a first movement sensing unit, to sense 3D movement (i.e. in the three axes X, Y, Z);
 a force sensing unit to sense the force exerted by the recovery element on the hitch
 a first processor, to receive the movement and force data sensed by the first movement sensing unit and the force sensing unit, respectively, and to generate data about the force applied by the subject when performing the action and direction of movement data;
 a data transmission unit, of the kind Bluetooth, to send the data generated by the first processor wirelessly; and a first battery, to power the first movement sensing unit, the force sensing unit, the first processor and the data transmission unit; and first means of closure, to close the belt to a required dimension.

As a second aspect, the invention describes a system for correcting the force and movement of the action performed by the subject, preferably focused on musculoskeletal rehabilitation, which includes the device described previously.

The system additionally includes a number of other component parts, including the following:

at least one database, which in turn contains:
   a personal profile of the subject, with information about the subject; and
   exercise files, comprising prescribed data on the actions of the subject, where the data includes, for each action: data on one or more prescribed positions of the subject while performing the action; and data on force applied by the subject during the action;
an access kit, to allow the subject to remotely access the personal profile, and that comprise:
a second processor to receive data from the data transmission unit and generate: representative data of visual representations of the position of the subject schematically performing the action; and force data applied by the subject while performing the action;
display means to show, based on the data generated by the second processor, schematic visual representations of the subject performing the action;
a comparator, to compare the prescribed data of the actions with the data generated by the second processor, to determine whether the positions of the subject and force carrying out the actions by the subject are in a pre-established relationship with the prescribed positions and force for the actions; and
means of warning to issue a real-time warning in the event that the positions of the subject and the force performing the actions do not maintain the pre-established relationship with the prescribed positions and force of the actions.

The second processor can be part of the first sensing module, rather than part of the access equipment. In particular, the second processor may be the same as the first processor.

Preferably, the database also includes video files with recordings of rehearsal sessions, in which the subject rehearses the actions to learn how to perform them.

As a third aspect, the invention refers to a method for correcting the force and displacement of the action, using the above-mentioned system.

The method comprises the following steps:
record, in a database, prescribed action data, including data on at least one prescribed position of the subject performing the action, and prescribed force data on the subject performing the action;
the subject connects remotely, through an access computer, to a personal profile, from which he or she accesses action files containing prescribed action data;
the subject places the device referred to previously to perform the actions and begins to perform an action;
the data transmission unit sends movement and force data to a second processor of the access equipment, which generates: representative data of schematic visual representations of the position of the subject performing the action; and force data applied by the subject while performing the action;
display means of the access equipment shows, based on the data generated by the second processor, schematic visual representations of the subject performing the action;
a comparator compares the prescribed action data with the data generated by the second processor to determine whether the positions of the subject and the force performed by the subject maintain a pre-established relationship with the prescribed positions and force for the actions; and
warning means issue a real-time warning in case the positions of the subject and the force when performing the actions do not maintain the pre-established relationship with the prescribed positions and force of the actions.

Preferably, video files are also recorded in the database where the subject is shown to perform the action in rehearsal sessions, where the video files are shown by the visualization means, as well as the schematic visual representations of the subject performing the action.

As indicated previously, preferably, the subject is a patient in musculoskeletal rehabilitation, as well as actions are rehabilitation exercises. In particular, as an example, rehearsal sessions are rehabilitation rehearsal sessions in which the patient performs rehabilitation exercises in the presence of a physiotherapist, to learn how to perform the exercises and to have a support tool to perform the exercises on their own, for example, at home.

DESCRIPTION OF THE DRAWINGS

To complement the description that is being made and in order to help a better understanding of the characteristics of the invention, according to a preferential example of practical embodiment of the same, is accompanied as an integral part of this description, a set of drawings in which with illustrative and not restrictive character, the following has been represented.

PREFERENTIAL EMBODIMENT OF THE INVENTION

Figure 1:
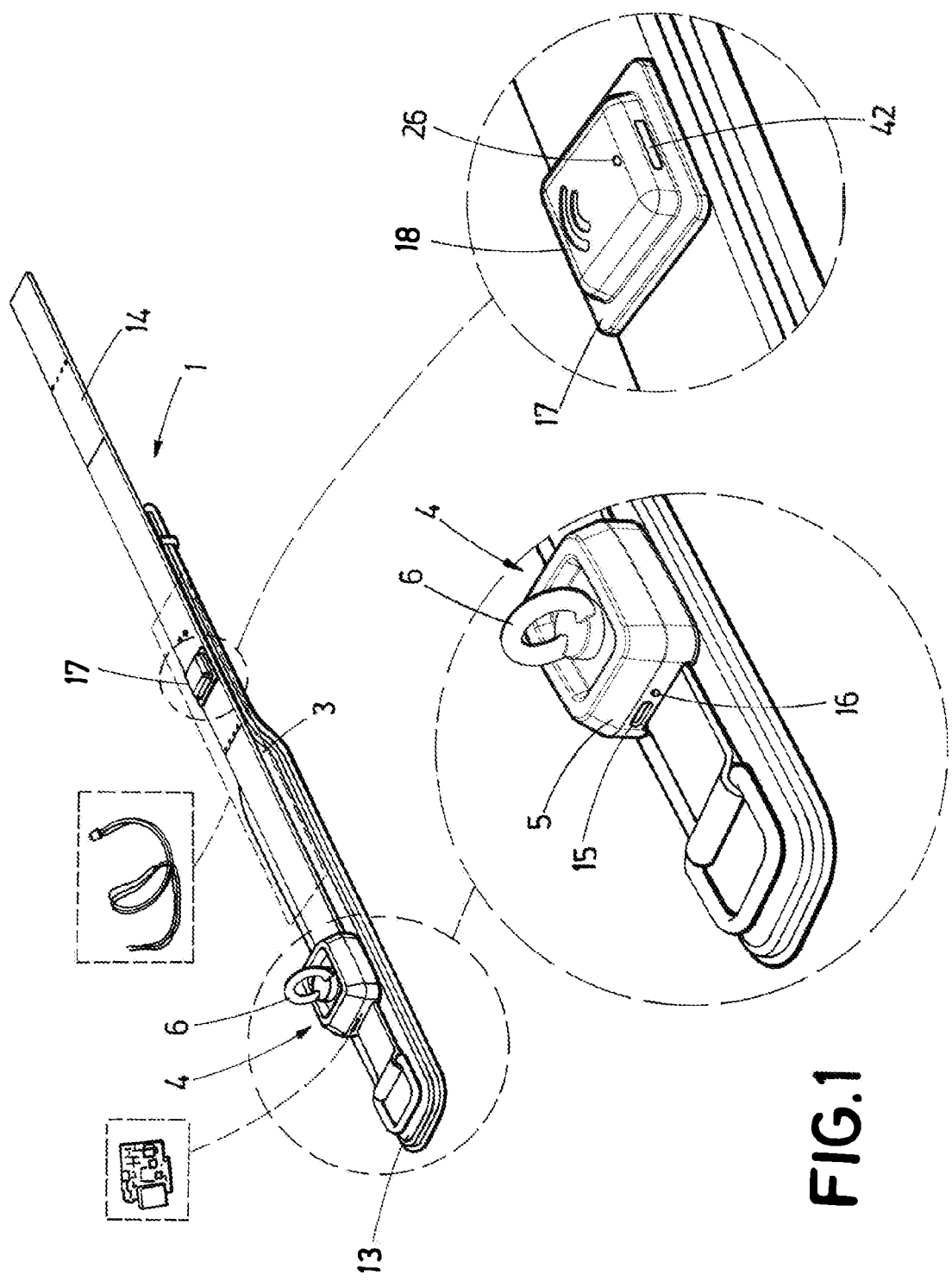
FIG. 1.—Shows an example of the embodiment of the present invention.
Figure 2:
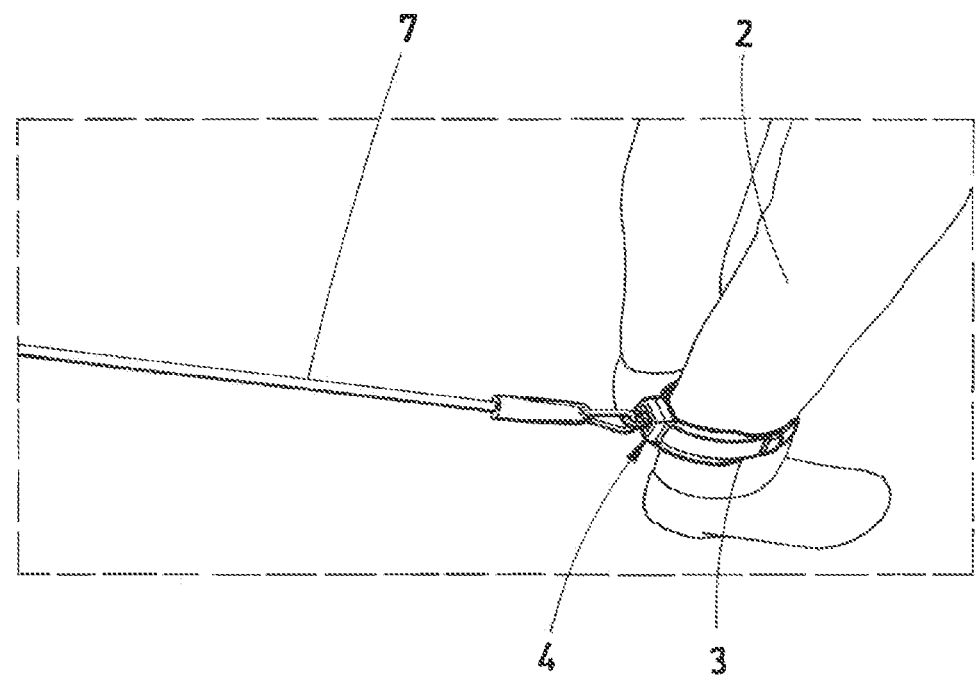
FIG. 2.—Shows an example of the use of the embodiment of FIG. 1.
Figure 3:
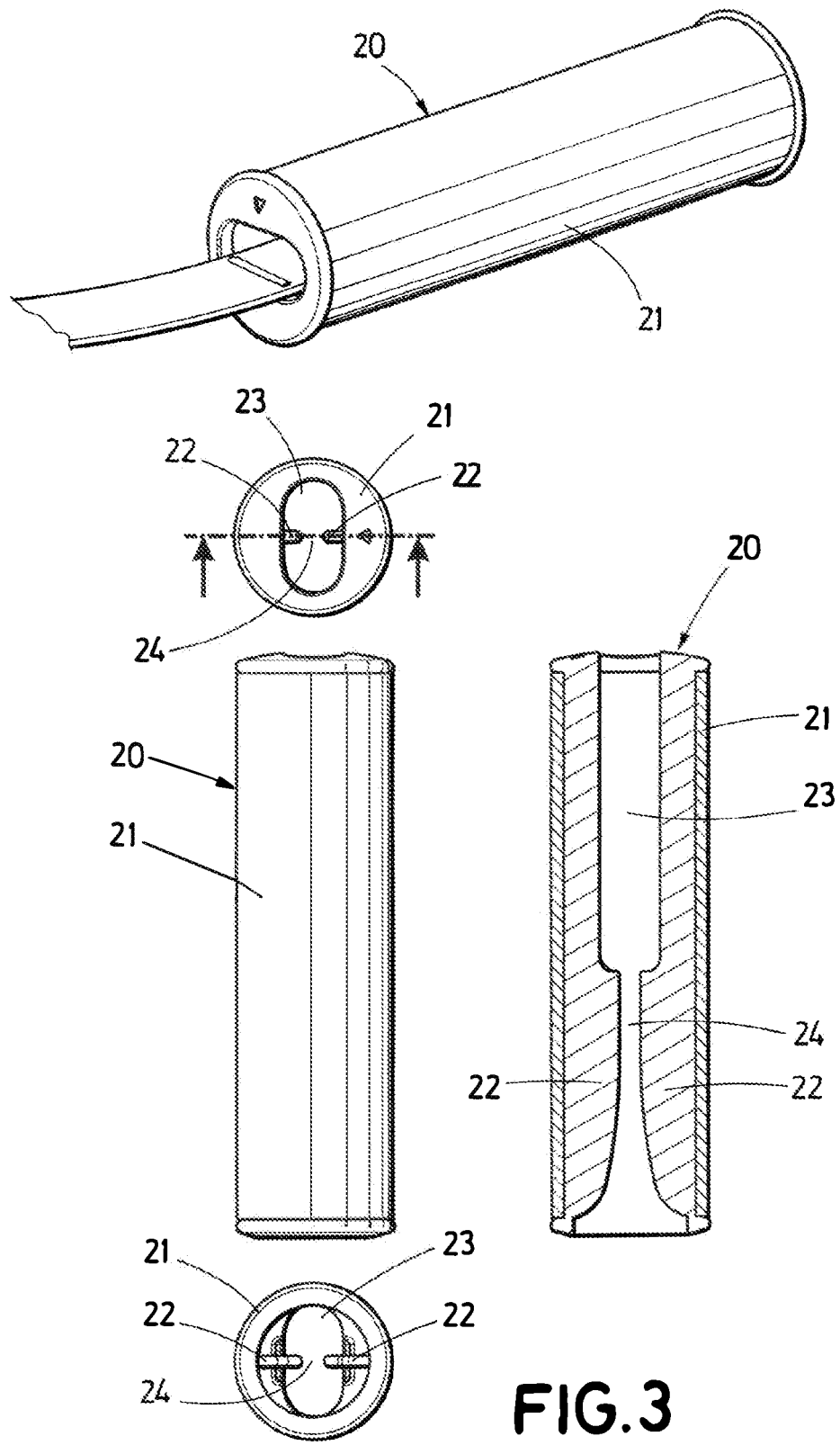
FIG. 3.—Shows an example of a handle according to a second embodiment.
Figure 4:
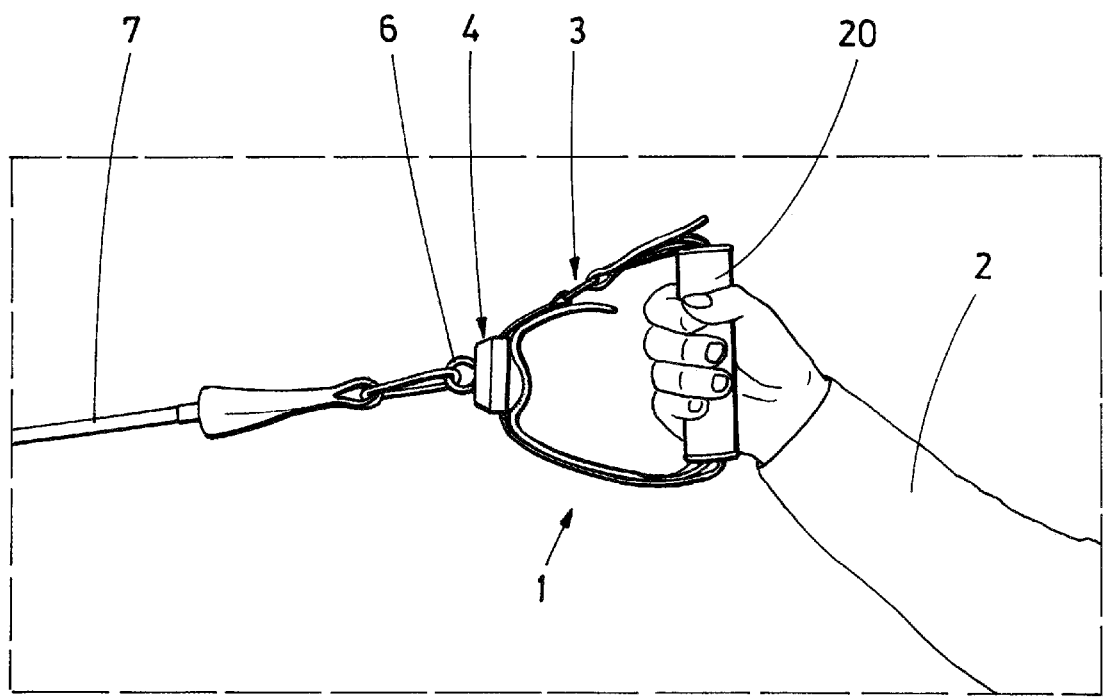
FIG. 4.—Shows an example of the use of the handle in FIG. 3.
Figure 5:
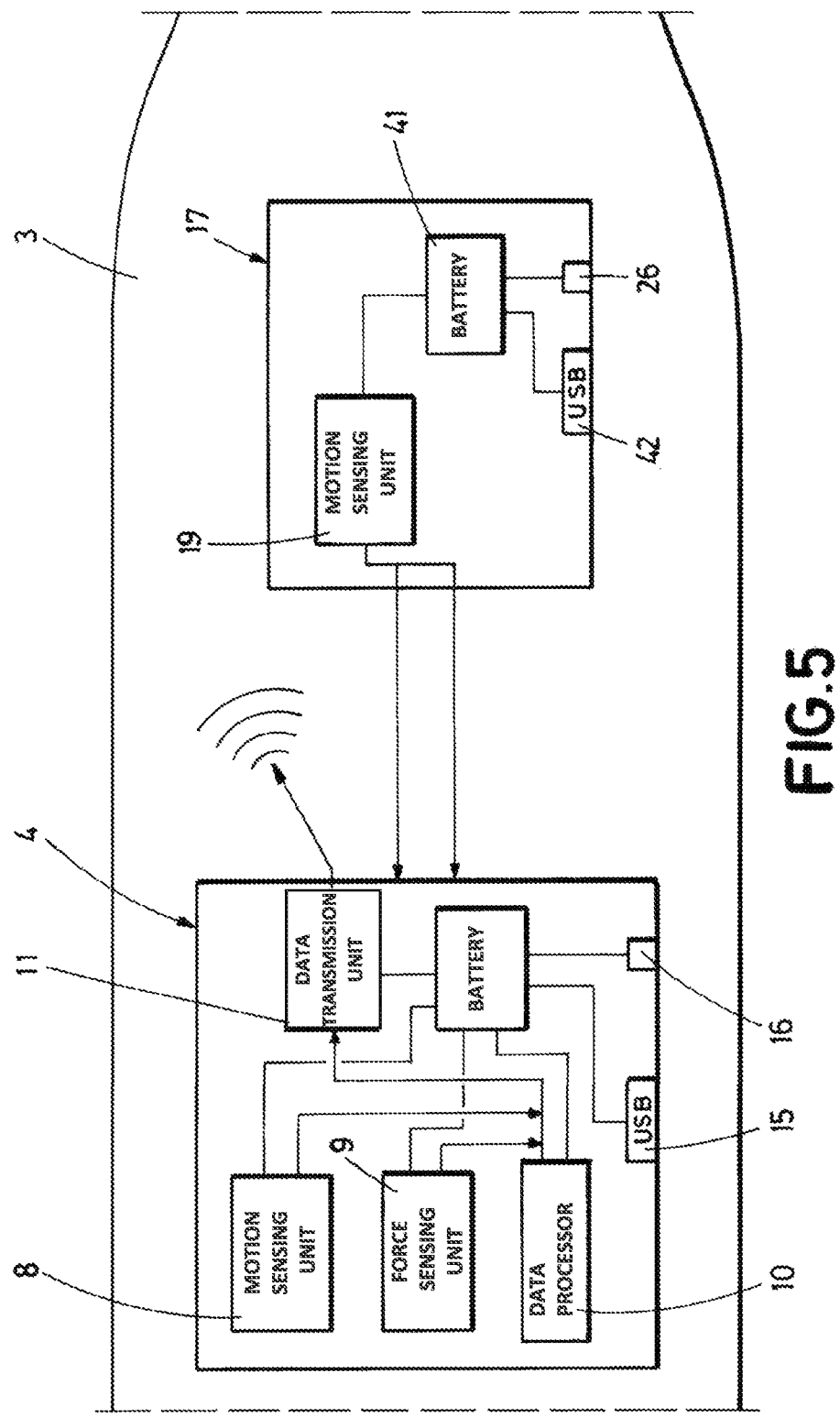
FIG. 5.—Shows a wiring diagram of the embodiments of FIGS. 1-4.
Figure 6:
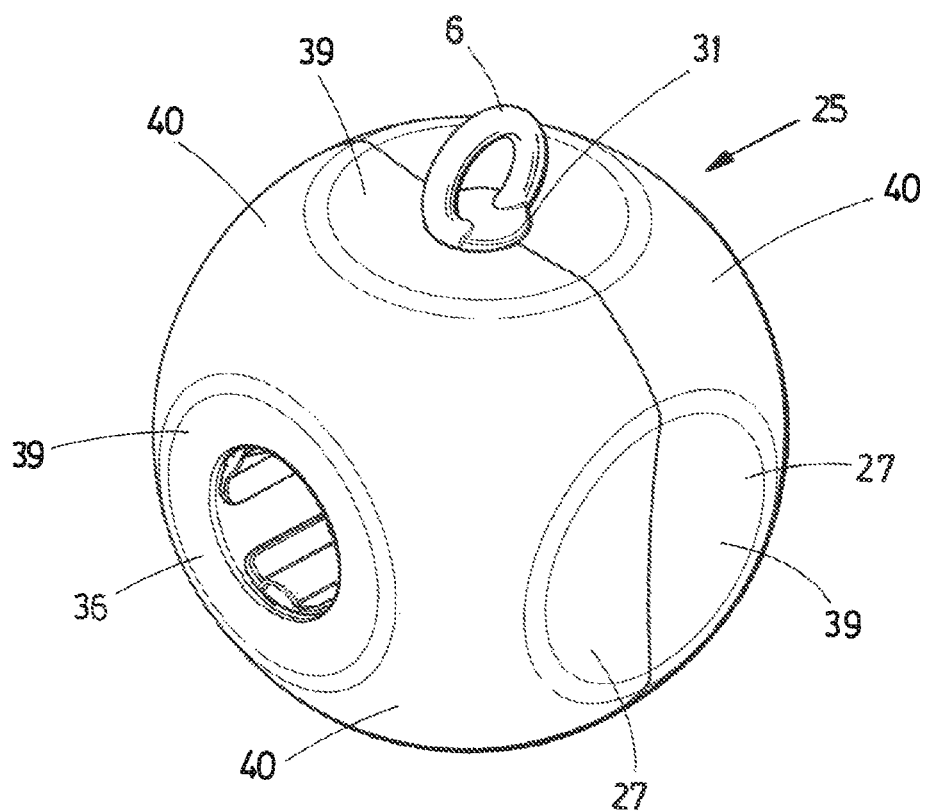
FIG. 6.—Shows a view of an accessory according to a third embodiment.
Figure 7:
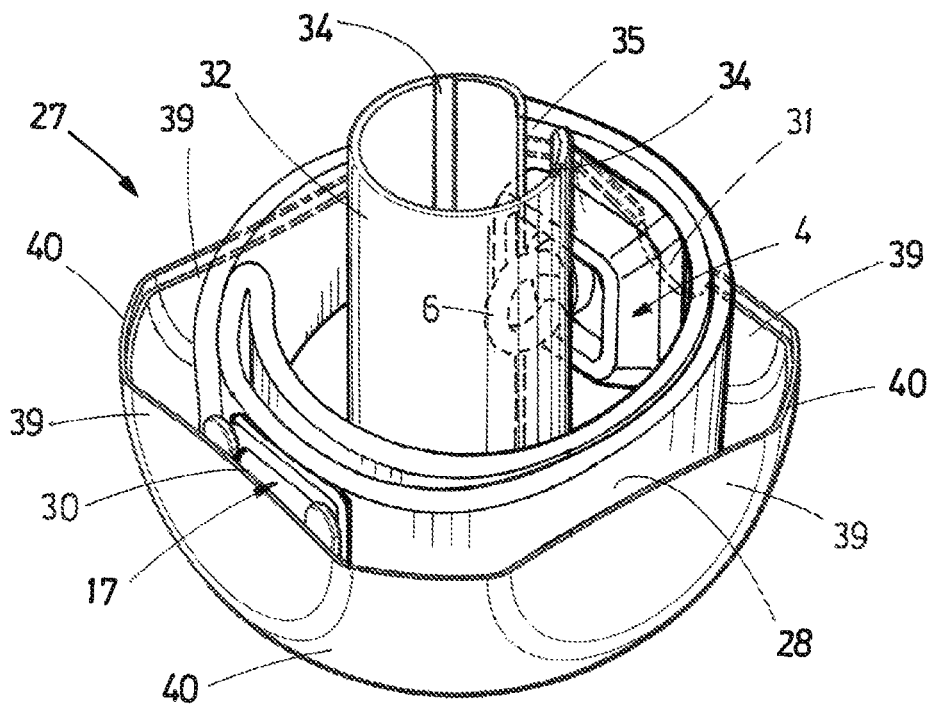
FIG. 7.—Shows the inside of one of the portions of the accessory in FIG. 6.
Figure 8:
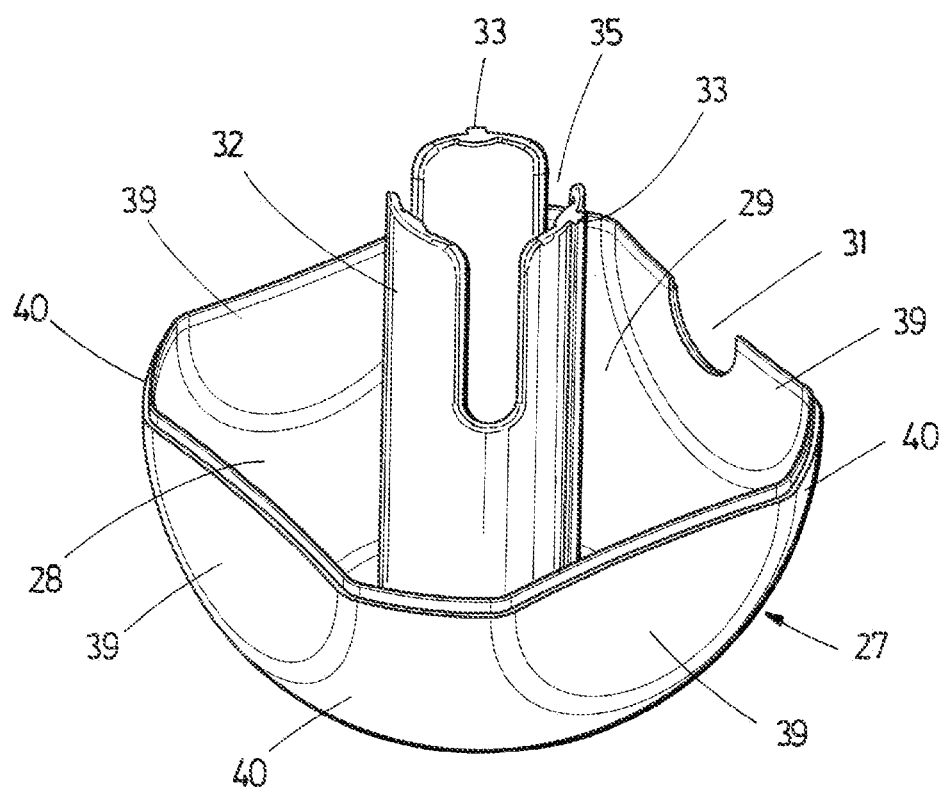
FIG. 8.—Shows a view of another of the portions that make up the accessory in FIG. 6.
Figure 9:
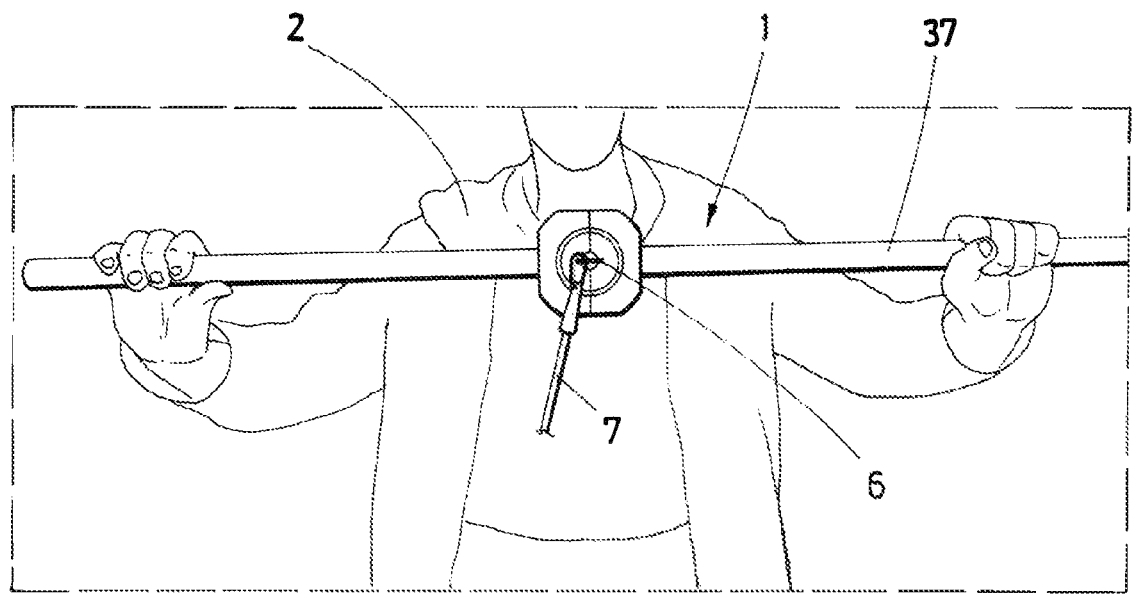
FIG. 9.—Shows an example of the use of the accessory by means of two rods.
Figure 10:
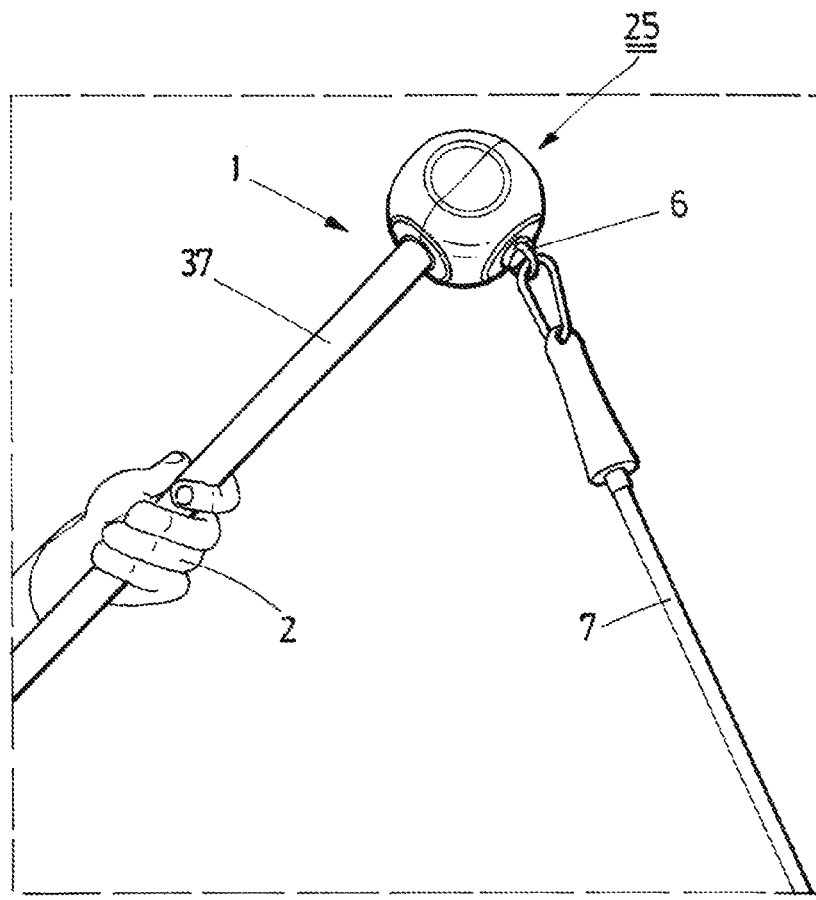
FIG. 10.—Shows another example of using the accessory with just one rod.
Figure 11:
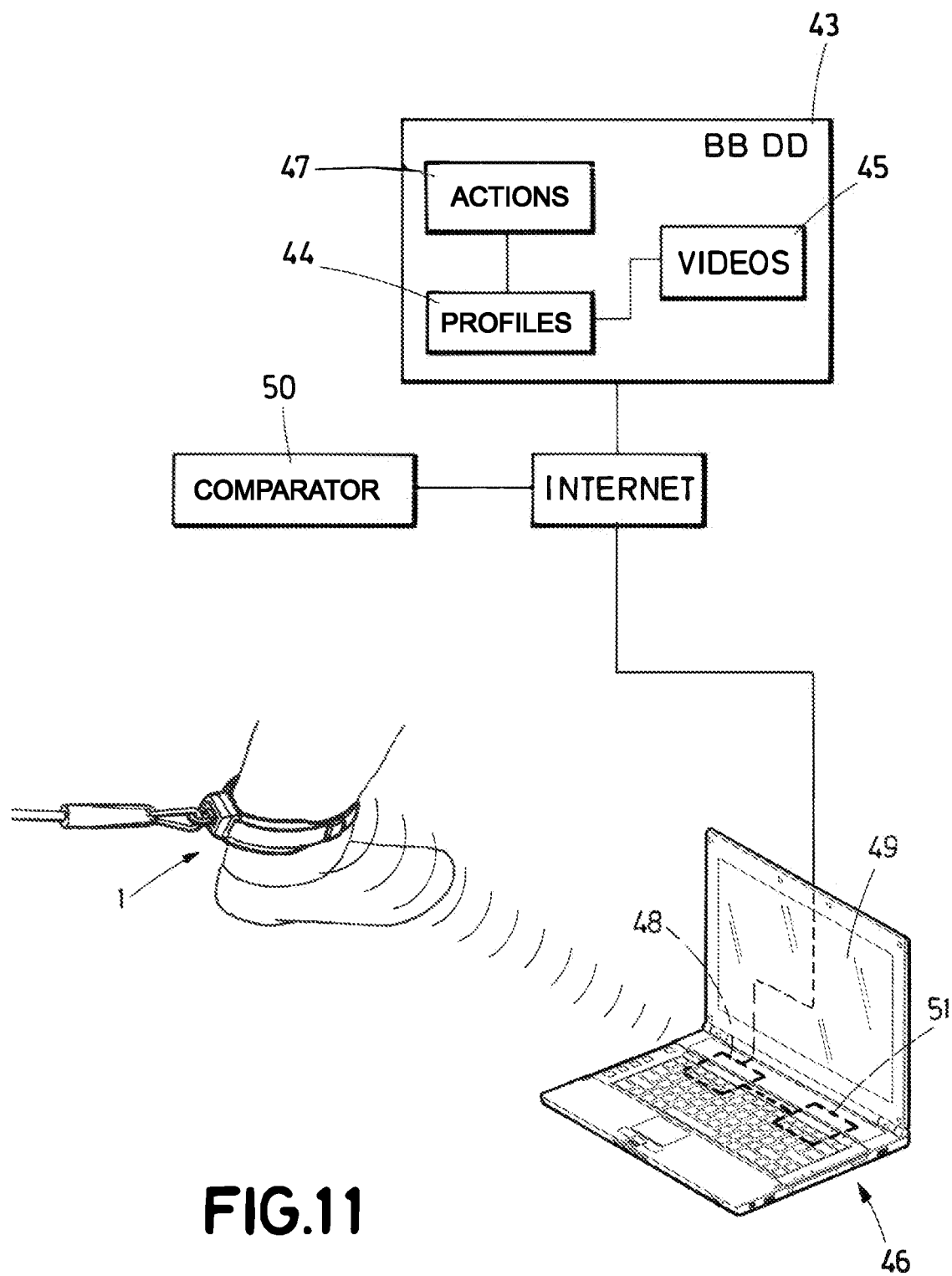
FIG. 11.—Shows a schematic view of the system of the invention.

A detailed description of several examples of preferred embodiments of the object of the invention is given below with the help of the previously mentioned FIGS. 1-11.

According with a first aspect, the invention refers to a device (1) for sensing force and movement in an action performed by a subject (2), where in particular, the example describes a case in which the subject (2) is a patient (2) in musculoskeletal rehabilitation, so that the action is an action of a rehabilitation exercise.

The device (1) comprises a belt (3) on which is mounted a first sensing module (4), which also comprises a first housing (5), which protrudes from the belt (3) and, mounted on the first housing (5), the following elements:

- a hitch (6), intended to be connected to a recovery element (7), such as a spring, which exerts a recovery force when activated by the patient (2);
- a first motion sensing unit (8), to sense 3D movement (meaning in the three axes X, Y, Z);
- a force sensing unit (9) to sense the force exerted by the recovery element (7) on the hitch (6);
- a first processor (10), to receive motion and force data sensed by the first motion sensing unit (8) and the force sensing unit (9), respectively, and to generate force data applied by the subject (2) when performing the action and motion direction data;
- a data transmission unit (11), for example of Bluetooth, for wireless transmission of data processed by the first processor (10); and
- a first battery (12) to power the first motion sensing unit (8), the force sensing unit (9), the first processor (10) and the data transmission unit (11).

The device (1) also includes the first means of closure (13, 14), so that the belt (3) can be closed to the required dimension. The first means of closure (13, 14) may include, as a more preferential example, a made in the belt (3) and a velcro fastener (14) located in portions of the belt (3). Other examples may be considered.

The first motion-sensing unit (8) may comprise one or more motion sensors, such as gyroscope, accelerometer and magnetometer. In addition, the first force sensing unit (9) can comprise at least one force sensor, such as a strain gauge.

The first housing (5) may also include a first USB port (15) for charging the first battery (12). The first housing (5) may also include a first indicator light (16), for example, of the LED type, to indicate the status of the first motion sensing unit (8), in particular the motion sensor(s). The status can be: off, standby, measuring, or loading.

The device (1) described previously is preferably intended for musculoskeletal rehabilitation, as explained next. In particular, the first means of closure (13, 14) allow the belt (3) to embrace, completely or at least partially encircling some area of the body of the patient (2), for example: ankle, calf; thigh, waist, chest, neck, forehead, wrist, forearm, arm, shoulder, etc. With the belt (3) encircling a selected part of the patient's body (2), and the recovery element (7) mounted on the hitch (6), the patient (2) proceeds to perform a prescribed rehabilitation movement, with which the first sensing module (4) is moved and the recovery element (7) is alternately tensioned and loosened. The displacement of the first sensing module (4) and the force of the recovery element (7) are measured and processed to generate movement direction data and force data, respectively, which are sent wirelessly to a component where, as will be explained later, the movement and force are analyzed and used to improve the feedback that the patient (2) gets at the time of exercise, which makes rehabilitation therapy more effective (2). The hitch (6) is suitable for connecting various types of recovery element (7), such as a spring, elastic band or elastic cord.

Preferably, on the belt (3) a second detection module can be additionally mounted, which comprises a second housing (18), which also protrudes from the belt (3), and in which a second motion sensing unit is hosted (19). The second movement-sensing unit (19) is connected by cable, or wirelessly, with the first motion-sensing unit (8), to send the movement data to the first processor (10), and which can be sent by the data transmission unit (11).

Analogous to what has been explained above for the first sensing module (4), the second movement-sensing unit (19) can comprise one or more motion sensors, such as gyroscope, accelerometer and magnetometer. The second housing (18) may also include a second indicator light (26), for example, of the LED type, to indicate the status of the second motion sensing unit (19), in particular the motion sensor(s). The status can be: off, standby, measuring, or load. On the other hand, the second sensing module (17) can include a second battery (41) to power the second motion sensing unit (19) and the second indicator light (26). Finally, the second housing (18) can be equipped with a second USB port (42) to charge the second battery (41).

Likewise, the device (1), equipped with the second sensing module (17), also includes a handle (20), which can be connected to the belt (3), as explained next. The handle (20) comprises a handle body (21), and fixing means (22) for attaching the belt (3) to the handle body (21), with the second sensing module (17) attached to the handle body (21). According to a preferential example, the handle body (21) is hollow, thus comprising a through hole (23) longitudinally extending to house one end of the belt (3) closer to the second sensing module (17) wherein the fixing means (22) comprise two fins (22) opposed extending inside of the through hole (23), leaving an intermediate space (24) which allows the second sensing module (17) to be held inside the through hole (23), solidly connected to the handle body (21), so that the second sensing module (17) describes the movement relative of the handle (20).

The following explains the use of the above-described method, which includes the second sensing module (17) and the handle (20). Once the belt has been closed (3) using the first means of closure (14, 15), and having connected the recovery element (7), the patient (2) can, by grasping the handle (20) with one or both hands, activate the device (1) to perform rehabilitation exercises as explained above, where the force sensing unit (9) registers the force of the recovery element (7), as well as the first movement sensing unit (8) senses the movement of the first sensing module (4). The additional use of the handle (20), combined with the second sensing module (17), provides the patient (2) with a rehabilitation, mainly of the upper body, in which the second sensing module (17), which is solidly connected to the handle body (21) and therefore to the patient's hand or hands (2), for example the wrist of the patient (2), also allows separate sensing of twisting movements of the wrists of the patient (2). As will be explained later, when the movements captured by both sensing modules (4, 17) are analyzed, it is determined whether there has been rotation of the wrists, which in some rehabilitation exercises is necessary and in others is inconvenient, which makes it possible to evaluate whether the patient (2) is performing the exercise correctly.

Preferably, the device (1) may also include an accessory (25), which allows additional exercises to be performed with the upper body. In particular, the accessory (25) comprises two hollow portions (27) which can be connected separately by means of second closure means.

The portions (27) have an inner first accommodation (28) to house the belt (3) and a second accommodation (29) and a third accommodation (30), also inner, to respectively house the first sensing module (4) and the second sensing module (17) when the belt (3) is in the inner first accommodation (28). The accessory (25) also includes a first exterior opening (31) connected to the through hole (23). The second accommodation (29) is configured to allow, at will, the hitch (6) to protrude out of the opening (31) or into the through hole (23). The first opening (31) is made up of both portions (27) of the accessory (25).

Preferably, the second closure means can be configured to allow the portions (27) of the accessory (25) to be connected in a single relative orientation. According to a preferential example, the second means of closure comprise two prismatic or cylindrical bodies (32), both of which are hollow, which extend towards the opposed hollow portion (27). Both bodies (32) are nestable inside each other in a longitudinal direction. In order to allow the bodies (32) to fit in a single relative orientation, the bodies (32) they may have at least, in a longitudinal direction, one projection around the perimeter and at least one corresponding first slot (34) For example, one of the bodies (32) has two first inner longitudinal slots (34), while the other body (32) has two outer longitudinal slots (33), corresponding to the first slots (34). In addition, the two bodies (32) may have second longitudinal slots (35) which pass through the entire thickness of the bodies (32), as well as from the free ends of the bodies (32), and which are superimposed when the first housing (5) is mounted, to allow the hitch (6) to be housed inside the bodies (32) when it does not protrude from the first opening (31).

The accessory (25) also includes two second openings (36), one in each of the portions (27), along the inside of the bodies (32). The device (1) additionally includes at least one rod (37), which can be inserted through the second openings (36) to pass through the accessory (25) and allow the patient (2) to perform exercises by grasping the rod (37) with one or both hands. The rod (37) and/or the second openings (36) may include stopping means (52) to prevent rotation and/or displacement of the rod (37).

With the hitch (6) protruding from the first opening (31), the recovery element (7) can be connected to the hitch (6), so that the use of the accessory (25) with the rod (37) allows the patient (2) to perform exercises whose strength and displacement can be sensed, as explained above.

Preferably, the rod (37) comprises modular sections (not shown) that can be connected to each other, for example, by screwing or threading, to define a rod (37) of various lengths. Also, the rod (37) can protrude widely from the sides of the accessory (25), which allows the patient (2) to grasp the rod (37) with both hands, one on each side, or it can protrude widely from only one side, so that only on that side the rod (37) can be grasped, also with only one hand or with both hands.

The incorporation of the accessory (25) also allows, with the hitch (6) housed in the third accommodation (30) inside the accessory (25), to perform a calibration of the motion sensing units (8, 19), as explained next.

In particular, the accessory (25) may be exteriorly limited by at least three flat faces (39), defined by normal directions, which, when taken as free vectors, are not coplanar. Preferably, three of the normal are mutually perpendicular. Even more preferably, the accessory (25) comprises six flat faces (6) which are parallel in pairs. For ease of handling, the accessory (25) may have rounded corners (40).

Before carrying out the previously mentioned calibration, the portions (27) forming the accessory (25) are separated; the first sensing module (4) is then fixed in the second accommodation (29) and, if necessary, the second sensing module (17) in the third accommodation (30), for example by placing the belt (3) in the first accommodation (28); finally, the two portions (27) are connected to close the accessory (25). A remote, wirelessly received instruction or a calibration switch (not represented), located on the belt (3), may be used to place the device (1) in "calibration" mode.

Calibration is carried out on the motion sensing unit(s) (8, 19), where applicable, by means of calibrations of its sensors, for example accelerometer and/or gyroscope and/or magnetometer. For calibration, the main core or the reference core comprises a calibration control unit (not shown) with specific software.

Typically, according to what is known from the state of the art, calibration requires moving (usually rotating) the motion sensing units (8, 19) to gather information about the orientation of their coordinate axes (X, Y, X). Advantageously, the use of the accessory (25), which can house inside the belt (3) with the motion sensing units (8, 19), as well as the flat faces (39) on which it can be supported, allows to perform the calibration on an easier and faster way, since it allows the coordinated axes (X, Y, Z) of the motion measurement units (8, 19) to be arranged very conveniently in any orientation. For example, a user can support the accessory (25) successively on each of its flat faces (39), and make it rotate with respect to the normal one to that flat face (39), in order to properly orient the coordinated axes (X, Y, Z). The accessory (25) can also be thrown into the air at random and rotated at the same time.

In accordance with a second aspect of the present invention, the device (1) referred to previously is part of a system for correcting force and motion of the action of a subject (2), particularly a patient (2) in rehabilitation, as explained below.

Likewise, according to a third aspect, the invention also refers to a method for correcting motion and force of action using the referred system.

The patient (2) with a joint injury goes to the doctor or rehabilitation center, where an assessment (diagnosis) of the injury is made. To diagnose, at least one motion meter (not shown) is first used to collect the movements of the affected joint. Preferably, two motion meters are used to evaluate a joint. One of the motion gauges is placed on the moving part of the joint, while the other motion gauge is placed on the fixed part of the joint, to act as a reference. For example, if the elbow is to be evaluated, the motion sensor that acts as a reference is located on the arm, between the elbow and the shoulder, and the other sensor is on the forearm.

Algorithms allow to analyze the data from the motion meters and visualize biometric parameters of the joint.

A rehabilitation physician, based on biometric parameter data, is able to determine the state of motion of the joint, which is determined by the joint's movement capabilities (and also limitations), as well as to determine the degree of damage, and thus to diagnose the specific extent of the injury and set rehabilitation goals.

A physiotherapist, using the biometric parameters of the rehabilitation of the diagnosis of the doctor, and using the device of the invention, in combination with the recovery element (7), and in any of its variants, depending on which joint is affected, exercises the joint and determines a therapy comprising prescribed rehabilitation exercises adapted to the needs of the patient (2), as well as establishing the parameters defining the rehabilitation exercises. In particular, the parameters may include: exercise name, exercise description, identification of the patient (2), one or more positions (for example a starting position, an end position, and one or more intermediate positions, if any) and force values, such as, for example, a force range to be applied, which determines the type of recovery element (7) to be used. The parameters of the prescribed exercises are stored, as part of exercise files (47), as data in a database (43), in which a profile (44) of the patient (2) is also stored.

Once the rehabilitation exercises and their parameters have been determined, the patient (2) undergoes one or more rehabilitation test sessions, in specialized facilities, where, under the physical supervision of the physiotherapist, the patient (2) performs the exercises that form part of his or her rehabilitation therapy. In this way, the physiotherapist can provide the patient (2) with face-to-face feedback, for example, correcting any errors made by the patient (2), or clarifying any doubts, in order to define the correct execution of the exercises. Rehabilitation rehearsal sessions can be recorded in video files (45), to remain available to the patient (2) in the profile (44) created for this purpose.

Rehabilitation exercises are intended to be performed by the patient (2) on his own, for example, at home, although in general the invention allows the patient (2) to perform rehabilitation exercises in a multitude of places, without the need for them to be specifically fitted out for rehabilitation exercises.

When the patient (2) wishes to perform the exercises on his own, he connects remotely from an access device (46), for example, a computer, a tablet, a mobile phone, etc., via the Internet, to a platform from which he can access his profile (44). From the profile (44), the patient (2) has access to the files of the rehabilitation exercises (47) designed for him/her, as well as to the video files (45) of the rehearsal sessions. The profile (44) is in the database (43), preferably in the Cloud or, in general, in some location where it can be updated by an administrator to guarantee plural access. The files with the exercises (47) and with the videos (45) are also preferably in the Cloud. It is not necessary, although it is possible, that the files are hosted within the profile (44); they may preferably be linked for access from the profile (44). For example, the files with the exercises (47) of all patients (2) can be stored in a general exercise file, so that the profile (44) of each patient (2) links only to the exercises that correspond to him/her.

Once the patient (2) has connected and the belt has been attached (3), and the force sensing unit(s) (9) and motion measurement unit(s) (8, 19) are operational, the patient (2) is ready to perform the prescribed rehabilitation exercises. The patient (2) begins one of the rehabilitation exercises. The data transmission unit (11) on the belt (3) wirelessly sends the force and displacement data of the rehabilitation action to a data reception unit on the access device (46).

A second processor (48), which is part of the access device (46), processes this data to generate: representative data of schematic visual representations of the position of the patient (2) by performing the rehabilitation exercise; and force data, which includes information on the force exerted. The representations are sent to display means (49), such as a monitor, of the access equipment (46), where a schematic representation of the patient (2) is shown in real time by performing the rehabilitation exercise, for example carrying the belt (3) and performing the movements related to the prescribed rehabilitation exercise. The second processor (48) can be part of the first detection module (4) instead of part of the access device (46). In particular, the second processor (48) may be the same as the first processor (10).

A comparator (50), which can be located on the access device (46), although preferably accessible from the access device (46) via the platform, also receives the data generated by the second processor (48) via the Internet and compares it with the prescribed exercise data to determine whether the position of the patient (2) and the force exercised during the exercise correspond in a predetermined way to those of the prescribed exercise. In particular, for example, the comparator (50) checks whether the force used is within the range of force recorded in the exercise files and whether the starting, intermediate and final positions of the action performed by the patient (2) correspond sufficiently (according to a pre-established criterion) to the positions recorded in the prescribed exercise files (47).

If the comparison is not satisfactory, a warning signal (visual and/or acoustic) is generated in real time by means of warnings (51). For example, a warning sound may be emitted, accompanied by an indication on the display means (49) that the exercise is not being carried out correctly. In particular, the indication on the display means (49) may include an explanatory text and/or an image representing which position is not being reproduced properly.

The display means (49) can optionally display, at the same time as the position of the patient (2) during the exercises, images from the video files (45) to help the patient (2), whether he or she is doing it correctly (no alert) or in the case of an alert.

The force and movement data are recorded and made available in the database for consultation by the rehabilitation physician and physiotherapist.

The use of this system/method provides the patient (2) with feedback in real time, which allows the patient (2) to perform the exercise with guarantees that he or she is doing it correctly, without having to deal with the therapist in person. This has a positive effect on rehabilitation, since:

The patient (2) has more confidence in the effectiveness of rehabilitation, which has a positive impact on his nor her motivation to continue the rehabilitation;

The doctor and physiotherapist can remotely access relevant information from the entire rehabilitation process, without having to deal with the patient (2) in person at all times.

Although the doctor is not present (tele rehabilitation), the patient (2) feels followed and cared for in a personalized way.

Rehabilitation for some injuries can be up to 60% faster.

The fact of been seen in the video helps the patient (2) to perform up to 40% better than if he does not have video.

The invention claimed is:

1. A device for sensing force and movement during an action performed by a subject, comprising:
   a belt;
   a first sensing module, mounted on the belt and comprising a first housing, which protrudes from the belt, and further comprising, mounted on the first housing:
      a hitch, to connect to a recovery component part, which exerts a recovery force on the hitch during the action performed by the subject;
      a first movement sensing unit, to sense 3D movement, that is in axes X, Y, Z of a reference system;
      a force sensing unit to sense the force exerted by the recovery component part upon the hitch;
      a first processor, to receive movement and force data detected by the first movement sensing unit and the force sensing unit, respectively, and to generate force data applied by the subject during the action performed and data on movement direction;
      a data transmission unit to wirelessly send the data generated by the first processor; and a first battery to power the first movement sensing unit, the force sensing unit, the first processor and the data transmission unit; and first closing elements, to close the belt to a required dimension;

a second sensing module mounted on the belt, comprising a second housing, which also protrudes from the belt, and which houses a second movement sensing unit, connected by wire or wirelessly to the first movement sensing unit to send movement data to the first processor, so that said data is configured to be sent by the data transmission unit, wherein the device further comprises:
  a handle, connectable with the belt, and which in turn includes:
    a handle body, which is hollow and comprises a through hole passing longitudinally, to house one end of the belt which is closer to the second sensing module; and
    a fixing element for attaching the belt to the handle body, which comprise two fins extending oppositely inside of the through hole, to create an intermediate space, which is configured to retain the second sensing module inside the through hole, solidly connected to the handle body.

2. A system to correct the movement and force of the action of a subject, which comprises the device according to claim 1, and further comprising:
  at least one database containing:
    a personal profile of the subject, with information referred to the subject; and
    action files, comprising prescribed data about the actions of the subject, wherein the data comprises, for each action: data about one or more prescribed positions of the subject while performing the action; and data about force applied by the subject during the action;
  an access device, to allow the subject to remotely access the profile, and that comprises:
    a second processor to receive data from the data transmission unit and generate: representative data of schematic visual representations of the position of the subject performing the action; and data about the force applied by the subject while performing the action;
    a monitor to show, based on the data generated by the second processor, schematic visual representations of the subject performing the action;
  a comparator, to compare the prescribed data of the actions with the data generated by the second processor, to determine whether the positions of the subject and the force for carrying out the actions by the subject maintain a pre-established relationship with the prescribed positions and force for the actions; and
  at least one warning element to issue a real-time warning in the event that the positions of the subject and the force performing the actions do not maintain the pre-established relationship with the prescribed positions and force of the actions.

3. The system according to claim 2, wherein the database additionally comprises video files with recordings of rehearsal sessions, in which the subject performs the actions.

4. A device for sensing force and movement during an action performed by a subject, comprising:
  a belt;
  a first sensing module, mounted on the belt and comprising a first housing, which protrudes from the belt, and further comprising, mounted on the first housing:
    a hitch, to connect to a recovery component part, which exerts a recovery force on the hitch during the action performed by the subject;
    a first movement sensing unit, to sense 3D movement, that is in axes X, Y, Z of a reference system;
    a force sensing unit to sense the force exerted by the recovery component part upon the hitch;
    a first processor, to receive movement and force data detected by the first movement sensing unit and the force sensing unit, respectively, and to generate force data applied by the subject during the action performed and data on movement direction;
    a data transmission unit to wirelessly send the data generated by the first processor; and
    a first battery to power the first movement sensing unit, the force sensing unit, the first processor and the data transmission unit; and
  first closing elements, to close the belt to a required dimension;
  a second sensing module mounted on the belt, comprising a second housing, which also protrudes from the belt, and which houses a second movement sensing unit, connected by wire or wirelessly to the first movement sensing unit to send movement data to the first processor, so that said data is configured to be sent by the data transmission unit,
  wherein the device further comprises:
    an accessory with:
      two hollow portions separately connectable to each other, by means of a second closing element;
      an inner first accommodation, defined in the hollow portions, to house the belt;
      an inner second accommodation, defined in the hollow portions, to house the first sensing module;
      an inner third accommodation, defined in the hollow portions, to house the second sensing module, when the belt is in the first accommodation; and
      an outer first opening, which is configured by the two hollow portions and leads to the through hole; wherein the inner second accommodation is configured to allow the hitch to protrude from the outer first opening or to be stored within the through hole.

5. The device according to claim 4, wherein the second closing element is configured to connect the hollow portions of the accessory in a single relative orientation of the two hollow portions.

6. The device according to claim 5, wherein the second closing element comprises, in each of the hollow portions, respective hollow bodies, prismatic or cylindrical, which extend towards the through hole, wherein both hollow bodies are nestable one inside the other in the longitudinal direction, and the hollow bodies have perimetrally, in the longitudinal direction, at least one protrusion and at least one corresponding first slot.

7. The device according to claim 6, wherein the two hollow bodies further comprise at least one second slot longitudinally traversing from a free end of each of the hollow bodies and defined through the full thickness of the hollow bodies, thus allowing the hitch to be placed inside the hollow bodies when it does not protrude from the first opening when the first housing is mounted.

8. The device according to claim 4, further comprising:
Two second openings wherein one is located in each of the hollow portions;
a rod, configured to be inserted through the second openings to pass through the accessory and to allow the subject to perform actions by grasping the rod with one or both hands.

9. The device according to claim 4, wherein the rod and/or the second openings include at least one stopping element, to avoid rotation and/or displacement of the rod.

10. The device according to claim 8, wherein the rod comprises modular sections configured to be connected to each other to lengthen the rod.

11. The device according to claim 4, wherein the accessory has an external surface comprising at least three flat faces, which are not coplanar.

12. The device according to claim 11, wherein three of the normal directions are mutually perpendicular.

13. A system to correct the movement and force of the action of a subject, which comprises the device according to claim 9, and further comprising:
at least one database containing:
a personal profile of the subject, with information referred to the subject; and
action files, comprising prescribed data about the actions of the subject, wherein the data comprises, for each action: data about one or more prescribed positions of the subject while performing the action; and data about force applied by the subject during the action;
an access device, to allow the subject to remotely access the profile, and that comprises:
a second processor to receive data from the data transmission unit and generate: representative data of schematic visual representations of the position of the subject performing the action; and data about the force applied by the subject while performing the action;
a monitor to show, based on the data generated by the second processor, schematic visual representations of the subject performing the action;
a comparator, to compare the prescribed data of the actions with the data generated by the second processor, to determine whether the positions of the subject and the force for carrying out the actions by the subject maintain a pre-established relationship with the prescribed positions and force for the actions; and
at least one warning element to issue a real-time warning in the event that the positions of the subject and the force performing the actions do not maintain the pre-established relationship with the prescribed positions and force of the actions.

14. The system according to claim 13, wherein the database additionally comprises video files with recordings of rehearsal sessions, in which the subject performs the actions.

* * * * *